United States Patent [19]

Patel

[11] 4,177,815
[45] Dec. 11, 1979

[54] CATHETER BALLOON STRUCTURE

[75] Inventor: Bhupendra C. Patel, Elgin, Ill.

[73] Assignee: The Kendall Company, Boston, Mass.

[21] Appl. No.: 874,072

[22] Filed: Feb. 1, 1978

[51] Int. Cl.$^2$ ............................................. A61M 25/00
[52] U.S. Cl. .................................. 128/349 B; 128/344
[58] Field of Search ............................ 128/348–351, 128/246, 344; 156/294

[56] References Cited

U.S. PATENT DOCUMENTS

| | | | |
|---|---|---|---|
| 2,547,758 | 4/1951 | Keeling | 128/349 B |
| 2,642,874 | 6/1953 | Keeling | 128/349 B |
| 3,112,748 | 12/1963 | Colburn | 128/349B |
| 3,734,100 | 5/1973 | Walker et al. | 128/349 B |
| 3,833,003 | 9/1974 | Taricco | 128/347 |
| 4,055,187 | 10/1977 | Patel et al. | 128/349 B |

*Primary Examiner*—Dalton L. Truluck
*Attorney, Agent, or Firm*—Powell L. Sprunger

[57] ABSTRACT

A catheter comprising, an elongated shaft having an inflation lumen extending along the shaft, and a pair of spaced annular ledges recessed from an outer surface of the shaft and defining spaced bonding surfaces extending circumferentially around the shaft. The shaft has an elongated section extending between the ledges and recessed from the bonding surfaces, with the shaft section defining an inner part of a cavity communicating with the inflation lumen intermediate the ledges. The catheter has an annular sleeve of elastic material having a thickness approximately equal to the distance between the bonding surfaces and the outer shaft surface adjacent the ledges, with the sleeve having a length approximately equal to the distance between remote ends of the ledges, and with opposed ends of the sleeve being bonded to the bonding surfaces circumferentially around the ledges.

5 Claims, 4 Drawing Figures

CATHETER BALLOON STRUCTURE

BACKGROUND OF THE INVENTION

The present invention relates to catheters, and more particularly to balloon structures for such catheters.

In the past, a various assortment of catheters, such as Foley catheters and endotracheal tubes, have been proposed for use in patients. In the case of urinary catheters, a conventional Foley catheter is normally constructed having a shaft defining a drainage lumen extending from a drainage eye adjacent a distal end of the shaft and an inflation lumen in the wall of the shaft, and having an expansible balloon overlying a distal portion of the shaft and communicating with the inflation lumen. In use, the distal end of the catheter is passed through the urethra until the drainage eye and balloon are located in the patient's bladder, and the balloon is inflated in the bladder to retain the catheter in the patient with a proximal end of the catheter located outside the patient's body. During catheterization, urine passes from the bladder through the drainage eye and lumen, and from the catheter through a drainage tube to a bag for collection therein.

A great majority of Foley catheters have been made from latex rubber through dipping techniques known to the art. However, a number of problems have been encountered with conventional latex catheters, such as difficulties in manufacture and delamination of the catheter sidewalls causing blockage in the inflation lumen. Accordingly, there has been a desire to construct catheters from materials which display superior properties both from the view of improved performance during use and permitting simplified manufacture to reduce cost. For example, it is preferred that the catheter shaft be made from a material which can be extruded in order to facilitate the manufacturing process and eliminate the delamination problems associated with dipped latex catheters. Additionally, the materials of the catheter shaft must be compatible with the patient's body to prevent deleterious results during use. The shaft, although flexible, should also have sufficient rigidity to permit placement of the catheter and prevent collapse of the shaft side walls. The balloon, of course, should be flexible and elastic to permit inflation in the patient's bladder, and preferably has a sufficient memory to assume its initial deflated configuration against the catheter shaft while being removed from the patient. It is desirable that the balloon may be formed by extrusion or molding techniques.

Assuming that a compatible adhesive exists for possibly differing materials of the balloon and shaft, such adhesive may be utilized to bond opposed ends of the balloon to spaced zones of the shaft. Of course, it is necessary to apply sufficient adhesive in the zones to obtain a satisfactory bond and close a cavity intermediate the zones for proper inflation of the balloon during use. However, the fabrication of catheters in this manner poses a dilemma for the manufacturer. If an insufficient amount of adhesive is placed between the balloon and shaft, then a satisfactory bond may not be obtained. Alternatively, if too much adhesive is used during bonding of the balloon, then the adhesive may spread laterally when the balloon is pressed onto the shaft, thus limiting the effective region of the balloon which may be inflated during use. Further, due to uncertainty in the width of the bonding zones which may vary circumferentially around the shaft, such bonding techniques may result in non-uniform balloons which inflate into differing shapes and at different pressures during use.

SUMMARY OF THE INVENTION

A principal feature of the present invention is the provision of a catheter with an improved and simplified balloon structure.

The catheter of the present invention comprises, an elongated shaft having an inflation lumen extending along the shaft, a pair of spaced annular ledges recessed from an outer surface of the shaft and defining spaced bonding surfaces of uniform width extending circumferentially around the shaft, and an annular section of the shaft extending between the ledges and recessed from the bonding surfaces, with the shaft section defining an inner part of a cavity communicating with the inflation lumen intermediate the ledges. The catheter has an annular sleeve of elastic material having a thickness approximately equal to the distance between the bonding surfaces and the outer shaft surface adjacent the ledges, with the sleeve having a length approximately equal to the distance between remote ends of the ledges. The catheter has means for bonding opposed ends of the sleeve to the bonding surfaces circumferentially around the ledges.

A feature of the present invention is that the shaft section is spaced from the bonding surfaces in order to prevent bonding of the balloon to the shaft section during fabrication of the catheter.

Another feature of the invention is that the ledges limit the effective surface area of the shaft which is bonded to the sleeve.

Thus, a feature of the present invention is that the balloon may be bonded to the shaft in a simplified manner while forming bonding zones of uniform width circumferentially around the shaft.

Yet another feature of the invention is that the bonded sleeve defines an inflatable region of uniform width which may be controlled to obtain uniform inflation characteristics among numerous assembled catheters.

Further features will become more fully apparent in the following description of the embodiments of this invention and from the appended claims.

DESCRIPTION OF THE PREFERRED EMBODIMENTS

Figure 1:
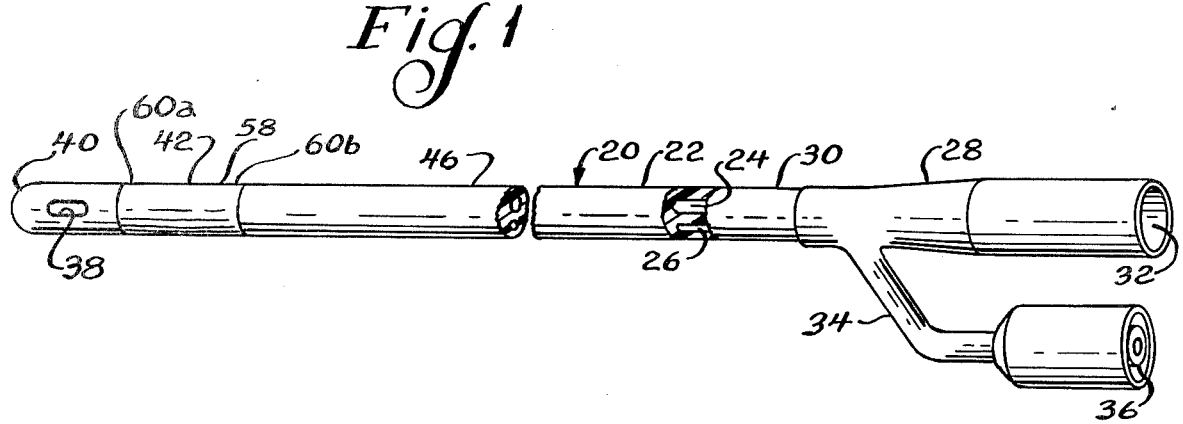
FIG. 1 is a fragmentary elevational view, partly broken away, of a catheter of the present invention.

Referring now to FIGS. 1-4, there is shown a urinary catheter generally designated 20 for draining urine from the bladder of a patient. Although the present invention will be described in connection with a urinary catheter, it will be understood that the principles of the present invention are equally applicable to other suitable catheters, such as endotracheal tubes. The catheter 20 has an elongated shaft 22 which in a preferred form is extruded. The shaft 22 has a main or drainage lumen 24 extending through the shaft and an inflation lumen 26 extending through a wall of the shaft. The catheter 20 may have a connector 28 secured to a proximal end 30 of the shaft 22, with the connector 28 having a channel 32 communicating with the drainage lumen 24 of the shaft 22. The connector 28 also has a side arm 34 defining a continuation of the inflation lumen 26 which communicates with valve means 36 at an outer end of the side arm 34. The catheter 20 has one or more drainage eyes 38 communicating with the main lumen 24 adjacent a distal end 40 of the catheter 20. Also, the catheter 20 has an inflatable balloon 42 adjacent the distal end 40 of the catheter shaft 22.

Figure 2:
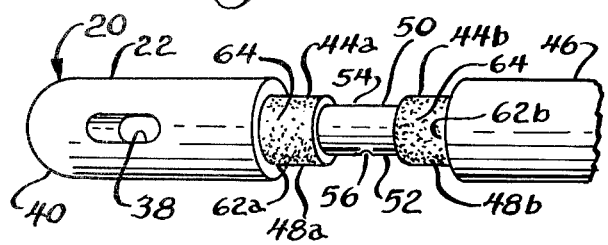
FIG. 2 is a fragmentary perspective view of a distal end of a catheter shaft prior to bonding a sleeve on the shaft.
Figure 3:
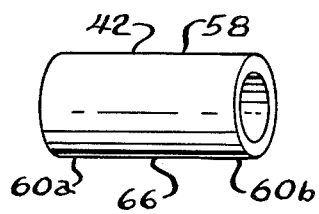
FIG. 3 is a perspective view of a sleeve for the catheter shaft of FIG. 2.
Figure 4:
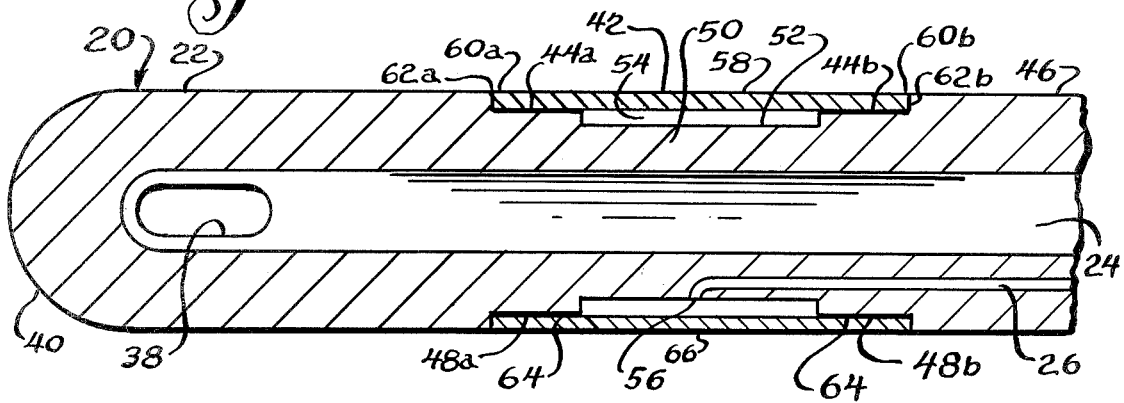
FIG. 4 is a fragmentary sectional view of the assembled catheter of FIG. 1.

With reference to FIGS. 2-4, the catheter shaft 22 has a pair of spaced annular ledges 44a and 44b which are recessed from an outer surface 46 of the shaft 22 and which define spaced bonding surfaces 48a and 48b of uniform width extending circumferentially around the shaft. The catheter shaft 22 also has an elongated annular section 50 extending between the ledges 44a and b and having an outer surface 52 recessed from the bonding surfaces 48a and b of the respective ledges 44a and b, with the shaft section 50 defining an inner part of a cavity 54 beneath the balloon which communicates with the inflation lumen 26 through an opening 56 intermediate the ledges 44a and b. The balloon 42 comprises an annular sleeve 58 of flexible and elastic material having a pair of opposed ends 60a and 60b. The sleeve 58 has a thickness approximately equal to the distance between the bonding surfaces 48a and b and the outer surface 46 of the shaft 22 adjacent the ledges, and a length approximately equal to the distance between remote ends 62a and 62b of the ledges 44a and b, respectively. In a suitable form, the ledges 44a and b and the shaft section 50 may be formed by grinding material from the shaft. The catheter balloon 42 and shaft 22 may be constructed from any suitable material, such as silicone or Kraton, a trademark of Shell Oil Company.

During fabrication, a suitable adhesive 64 may be spread uniformly over the bonding surfaces 48a and b of the ledges 44a and b, and the sleeve 58 may be placed over the shaft with the sleeve ends 60a and b located over the bonding surfaces 48a and b after which the sleeve ends 60a and b may be pressed against the ledges 44a and b to obtain a suitable bond. At this time, any excessive adhesive on the bonding surfaces 48a and b passes from the ledges 44a and b into the cavity 54 defined by the shaft section 50 intermediate the ledges 44a and b. Since the shaft section 50 remains spaced from a central section 66 of the sleeve 58 intermediate the ledges 44a and b, the ledges 44a and b and intermediate shaft section 50 serve to limit the effective width of the circumferential bonding zones between the sleeve and the shaft. In an alternative form, the opposed ends of the sleeve may be sealed to the ledges, such as by heat sealing, throughout the bonding surfaces. In both cases, the bonding zones may be readily formed of a uniform width equal to the width of the ledges 44a and b, thus resulting in a uniform width of the central section sleeve 66 circumferentially around the catheter. The effective width of the inflatable central section 66 may be controlled to obtain uniform shapes and inflation pressures of the balloons among the various constructed catheters during use. Thus, in accordance with the present invention uniform balloon structures may be obtained in a simplified manner to provide uniform inflation characteristics during use.

The foregoing detailed description is given for clearness of understanding only, and no unnecessary limitations should be understood therefrom, as modifications will be obvious to those skilled in the art.

I claim:

1. A catheter comprising, an elongated shaft having an inflation lumen extending along the shaft, a pair of spaced annular ledges recessed from an outer surface of the shaft circumferentially around the shaft and defining spaced recessed bonding surfaces extending circumferentially around the shaft, and an annular section of the shaft extending between said ledges and recessed from said bonding surfaces circumferentially around the shaft, with said shaft section defining an inner part of a cavity communicating with the inflation lumen intermediate said ledges, said catheter having an annular sleeve of elastic material having a thickness approximately equal to the distance between said bonding surfaces and the outer shaft surface adjacent said ledges, with said sleeve having a length approximately equal to the distance between remote ends of said ledges, and said catheter having means for uniformly bonding opposed ends of said sleeve to said bonding surfaces circumferentially around the ledges.

2. The catheter of claim 1 wherein the bonding means comprises adhesive interposed between said bonding surfaces and the opposed ends of said sleeve.

3. The catheter of claim 1 wherein said bonding means comprises a seal of the opposed ends of said sleeve to said bonding surfaces.

4. The catheter of claim 1 wherein said inflation lumen extends through a wall of the shaft intermediate said outer shaft surface and a drainage lumen extending through the shaft.

5. The catheter of claim 4 wherein said inflation lumen communicates with said cavity through an opening in said shaft section intermediate said ledges.

* * * * *